US006860855B2

(12) United States Patent
Shelby et al.

(10) Patent No.: US 6,860,855 B2
(45) Date of Patent: Mar. 1, 2005

(54) SYSTEM AND METHOD FOR TISSUE BIOPSY USING ULTRASONIC IMAGING

(75) Inventors: Jerod O. Shelby, West Richland, WA (US); Barbara A. Fecht, Richland, WA (US); Denis A. O'Connor, Newcastle, WA (US)

(73) Assignee: Advanced Imaging Technologies, Inc., Preston, WA (US)

( * ) Notice: Subject to any disclaimer, the term of this patent is extended or adjusted under 35 U.S.C. 154(b) by 0 days.

(21) Appl. No.: 09/988,868

(22) Filed: Nov. 19, 2001

(65) Prior Publication Data

US 2003/0097066 A1 May 22, 2003

(51) Int. Cl.$^7$ ................................ A61B 8/14
(52) U.S. Cl. ................................................ 600/459
(58) Field of Search .................... 600/407–471; 73/625, 626; 367/7, 11, 130, 138, 100; 128/916; 430/1–3; 359/22

(56) References Cited

U.S. PATENT DOCUMENTS

| | | | |
|---|---|---|---|
| 3,564,905 A | 2/1971 | Brenden et al. ............. 73/67.5 |
| 3,742,439 A | 6/1973 | Sheridon ................... 340/5 H |
| 3,879,989 A | 4/1975 | Brenden ................... 73/67.5 H |
| 3,911,729 A | 10/1975 | Collins ..................... 73/67.5 H |
| 3,937,066 A | 2/1976 | Green et al. ............. 73/67.5 R |
| 3,983,529 A | 9/1976 | Langlois .................... 340/5 H |
| 4,028,934 A | 6/1977 | Sollish ..................... 73/67.8 S |
| 4,075,883 A | 2/1978 | Glover ........................ 73/620 |
| 4,222,274 A | 9/1980 | Johnson ....................... 73/607 |
| 4,434,799 A | 3/1984 | Taenzer ...................... 128/660 |
| 4,478,481 A | 10/1984 | Fusek et al. ................ 350/3.83 |
| 4,531,410 A | 7/1985 | Crostack ...................... 73/603 |
| 4,662,222 A | 5/1987 | Johnson ....................... 73/602 |
| 5,179,455 A | 1/1993 | Garlick .......................... 359/9 |
| 5,212,571 A | 5/1993 | Garlick et al. ................. 359/9 |
| 5,235,553 A | 8/1993 | Garlick et al. ................. 367/7 |
| 5,329,202 A | 7/1994 | Garlick et al. .............. 310/334 |
| 5,329,817 A | 7/1994 | Garlick et al. ................ 73/605 |
| 5,740,268 A | 4/1998 | Nishikawa et al. .......... 382/132 |
| 5,796,003 A | 8/1998 | Sandhu et al. ................ 73/603 |
| 5,984,870 A | 11/1999 | Giger et al. ................. 600/443 |
| 5,999,836 A | 12/1999 | Nelson et al. ............... 600/407 |
| 6,032,673 A | 3/2000 | Savage et al. .............. 128/898 |
| 6,128,523 A | 10/2000 | Bechtold et al. ............. 600/411 |
| 6,353,576 B1 * | 3/2002 | Garlick et al. ................ 367/10 |

* cited by examiner

*Primary Examiner*—Ali Imam
(74) *Attorney, Agent, or Firm*—Seed IP Law Group PLLC (57) ABSTRACT

A tissue biopsy device uses ultrasonic imaging to guide the biopsy needle. An ultrasonic imaging device comprises three acoustically coupled chambers with an ultrasound transducer in a first chamber, at least a portion of an ultrasound detector in the second chamber and the portion of patient anatomy to be imaged placed in the third chamber, which is intermediate the first and second chambers. The three chambers are filled with an acoustically transmissive liquid. One or more of the end walls dividing the first and third chambers and second and third chambers may be movable to form compression plates that are used to retain the patient anatomy in a fixed position during the imaging and biopsy process. When a structure, such as a lesion, has been located, the imaging may be used to determine the precise location of the lesion in three dimensions. The ultrasonically transmissive fluid is drained from the central third chamber with ultrasonic coupling occurring through the ultrasonically transmissive compression plates and the imaged patient anatomy. This permits real-time imaging of the patient anatomy during the biopsy process. The three-dimensional coordinates are used to provide a manual guide for insertion of the biopsy needle. Light bars may be projected onto the external anatomy of the patient to indicate the desired point of entry of the biopsy needle. The physician may use the real-time imaging to view both the lesion and the biopsy needle. In an alternative embodiment, a biopsy needle may be automatically positioned at the location of the lesion by a three-dimensional positioning system.

29 Claims, 10 Drawing Sheets

SYSTEM AND METHOD FOR TISSUE BIOPSY USING ULTRASONIC IMAGING

BACKGROUND OF THE INVENTION

1. Field of the Invention

The present invention is directed generally to diagnostic imaging and more particularly, to a system and method for diagnostic imaging as a tool for performing biopsy.

2. Description of the Related Art

In biopsy or localization procedures it is necessary to ensure accurate placement and deployment of a biopsy needle, localization wire, or clip at the site of a lesion. Knowledge of lesion location prior to needle insertion and real-time image information to ensure probe trajectory along a direct line approach through the tissue to the targeted lesion is important. Conventional techniques, such as x-ray imaging, use radiation imaging techniques to guide the biopsy device to the targeted lesion. This technique may provide sufficient guidance for the biopsy procedure, but has the undesirable side affect of exposing the patient and the physician to undesirable radiation. Therefore, it can be appreciated that there is a significant need for imaging technology that will guide a biopsy device but avoid undesirable side affects. The present invention provides this and other advantages as will be apparent from the following detailed description and accompanying figures.

BRIEF SUMMARY OF THE INVENTION

The present invention is embodied in a system and method for biopsy using ultrasound imaging. In one embodiment, a multi-chambered tank is provided for ultrasonic imaging. The apparatus comprises a first chamber containing ultrasonically transmissive fluid with a portion of the patient anatomy positioned in the first chamber and the ultrasonic imaging apparatus being positioned in a location other than the first chamber. A display is provided to display the imaged portion of the anatomy to permit imaging of a structure from which a sample will be taken for biopsy. An aperture in the first chamber permits draining of the ultrasonically transmissive fluid to permit access to the structure from which a sample will be taken for biopsy.

In an exemplary embodiment, the ultrasonic imaging apparatus continues to generate an image during a biopsy procedure wherein the display displays the imaged portion of the anatomy and a biopsy device. In one embodiment, the ultrasonic imaging apparatus comprises an ultrasonic transducer. The system further comprises a second chamber containing ultrasonically transmissive fluid with the ultrasonic transducer being positioned within the second chamber. In yet another embodiment, the ultrasonic imaging apparatus comprises an ultrasonic detector and the system includes a third chamber containing ultrasonically transmissive fluid with at least a portion of the ultrasonic detector being positioned within the third chamber.

In another embodiment, the display provides an image in a predetermined focal plane of the structure from which a sample will be taken for biopsy. In this embodiment, the system further comprises a visual indicator of the predetermined focal plane to indicate the predetermined focal plane with respect to an external portion of the patient anatomy. The visual indicator may comprise a light bar projected onto the external portion of the patient anatomy. The system may also include a tracking system to determine the coordinates of the structure from which a sample will be taken for biopsy. In an embodiment where a lens system is used to focus on a predetermined focal plane, the display may display a two-dimensional image of the structure from which a sample will be taken for biopsy and the tracking system determines the coordinates in three-dimensional space using data related to the predetermined focal plane in the display image to determine the coordinates in a two-dimensional plane and using data related to the predetermined focal plane to determine the coordinates in a third dimension. The system may also comprise a robotic member to automatically position a biopsy device at the coordinates of the location of the structure from which a sample will be taken for biopsy.

In one embodiment, the system comprises first and second tanks filled with the ultrasonically transmissive fluid with the first tank containing the ultrasonic transducer and the second tank containing at least a portion of the ultrasonic detector. A third thank is positioned intermediate the first and second tanks and adapted to receive the portion of the patient anatomy to be imaged. The third tank is also filled with ultrasonically transmissive fluid. The system further comprises first and second endwalls to define boundaries between the first and third tanks and the second and third tanks, respectively, with the first and second endwalls being made from a material that is ultrasonically transmissive. The third tank may include an access panel to permit access to the portion of the patient anatomy to be imaged. A drain aperture may drain the ultrasonically transmissive fluid such that acoustical coupling between the ultrasonic transducer and the ultrasonic detector is maintained via the ultrasonically transmissive fluid in the first and second tanks and the portion of the patient anatomy to be imaged.

DETAILED DESCRIPTION OF THE INVENTION

The present invention is directed to an apparatus and method to perform a needle biopsy and localization interface between commercially available biopsy probes and an imaging system. In one embodiment, the intended biopsy probes are handheld devices that are guided manually by the operator or may be mechanically coupled to the imaging system. Alternatively, the system may be automated such that three-dimensional location information is provided to a robotic arm or similar device which automatically guides the biopsy probe to the intended location.

Figure 1:
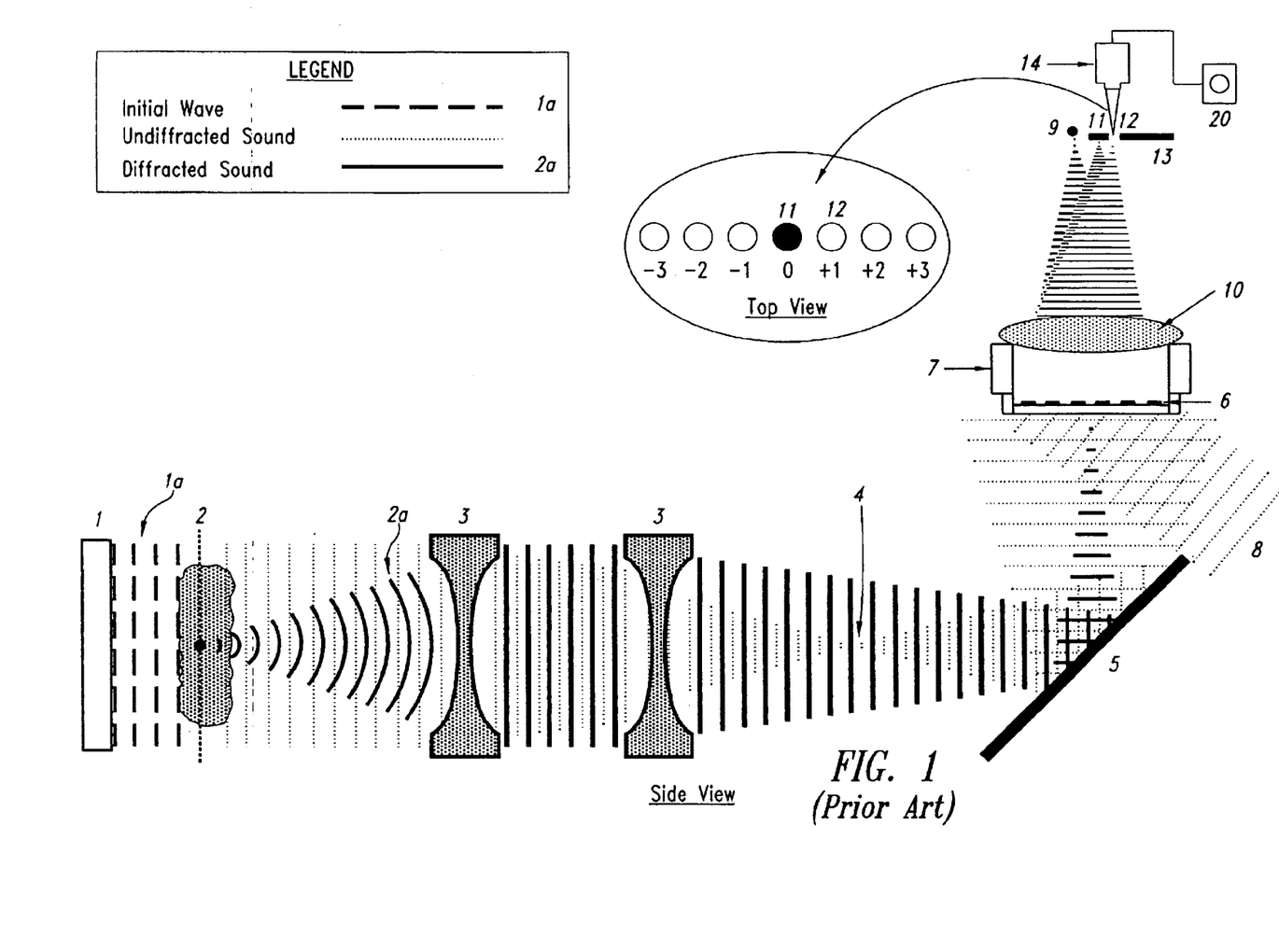
FIG. 1 is a functional block diagram illustrating the operation of a conventional through-transmitted wave acoustic ultrasound holography of prior art.

One embodiment of the imaging process can be that of through transmission acoustical holography. One such imaging system is described in U.S. Pat. No. 6,432,053 entitled "Process for Non-Invasively Determining the Dimensions of a Lesion," which is assigned to the assignee of the present invention and which is incorporated herein by reference in its entirety. Ultrasonic holography as typically practiced is illustrated in FIG. 1. A plane wave of sound 1a (i.e., ultrasound) is generated by a large area object transducer 1. Such a transducer is described in U.S. Pat. No. 5,329,202. The sound is scattered (i.e., diffracted) by structural points within the object. The scattered sound 2a from the internal object points that lie in a focal plane 2 are focused (i.e., projected) into a hologram detector plane 6 of a hologram detector 7. The focusing is accomplished by ultrasonic lens system 3, which focuses the scattered sound into the hologram detector plane 6 and the unscattered sound into a focal point 4. U.S. Pat. No. 5,235,553 describes ultrasonic lens that may be satisfactorily used for the ultrasonic lenses illustrated as the lens system 3 in FIG. 1. The ultrasonic lens system 3 also allows the imaging process to magnify the image (i.e., zoom) or change focus position. U.S. Pat. No. 5,212,571 illustrates a lens system that can magnify the image and change focus position and may be used satisfactorily for the lens system 3.

Since the focal point 4 of the unscattered sound is prior to the hologram detector plane 6, this portion of the total sound again expands to form the transparent image contribution (that portion of the sound that transmitted through the object as if it were transparent or semi-transparent). In such an application, an ultrasound reflector 5 is generally used to direct the object sound at a different angle, thus impinging on the hologram detector plane 6, which usually contains a liquid that is deformed by the ultrasound reflecting from the liquid-air interface. In an exemplary embodiment, the base of the hologram detector 7 is made to be parallel with the ground so that the thickness of the fluid below hologram plane 6 remains at a constant value.

When a reference wave 8 and the object wave are simultaneously reflected from the hologram detector 7, the deformation of the liquid-air interface is the exact pattern of the ultrasonic hologram formed by the object wave (1a combined with 2a) and the "off-axis" reference wave 8.

This ultrasonic hologram formed on the detector plane 6 is subsequently reconstructed for viewing by using a coherent light source 9, which may be passed through an optical lens 10, and reflected from the holographic detector plane 6. U.S. Pat. No. 6,353,576 describes a hologram detector suitable for use as the hologram detector 7 illustrated in FIG. 1. Other forms of detector may be used in place of the liquid surface hologram detector 7.

This reflected coherent light contains two components. The first component is light that is reflected from the ultrasound hologram that was not diffracted by the ultrasonic holographic pattern, which is focused at position 11 and referred to as undiffracted or zero order light. The second component is light that does get diffracted from/by the ultrasonic hologram is reflected at an "off-axis" angle from the zero order at position 12 and referred to as the "first order" image view when passed through a spatial filter 13. It is noted that this reconstruction method produces multiple diffraction orders each containing the ultrasonic object information. Note also both + and − multiple orders of the diffracted image are present and can be used individually or in combinations to view the optical reconstructed image from the ultrasonically formed hologram by modifying the spatial filter 13 accordingly.

Figure 2:
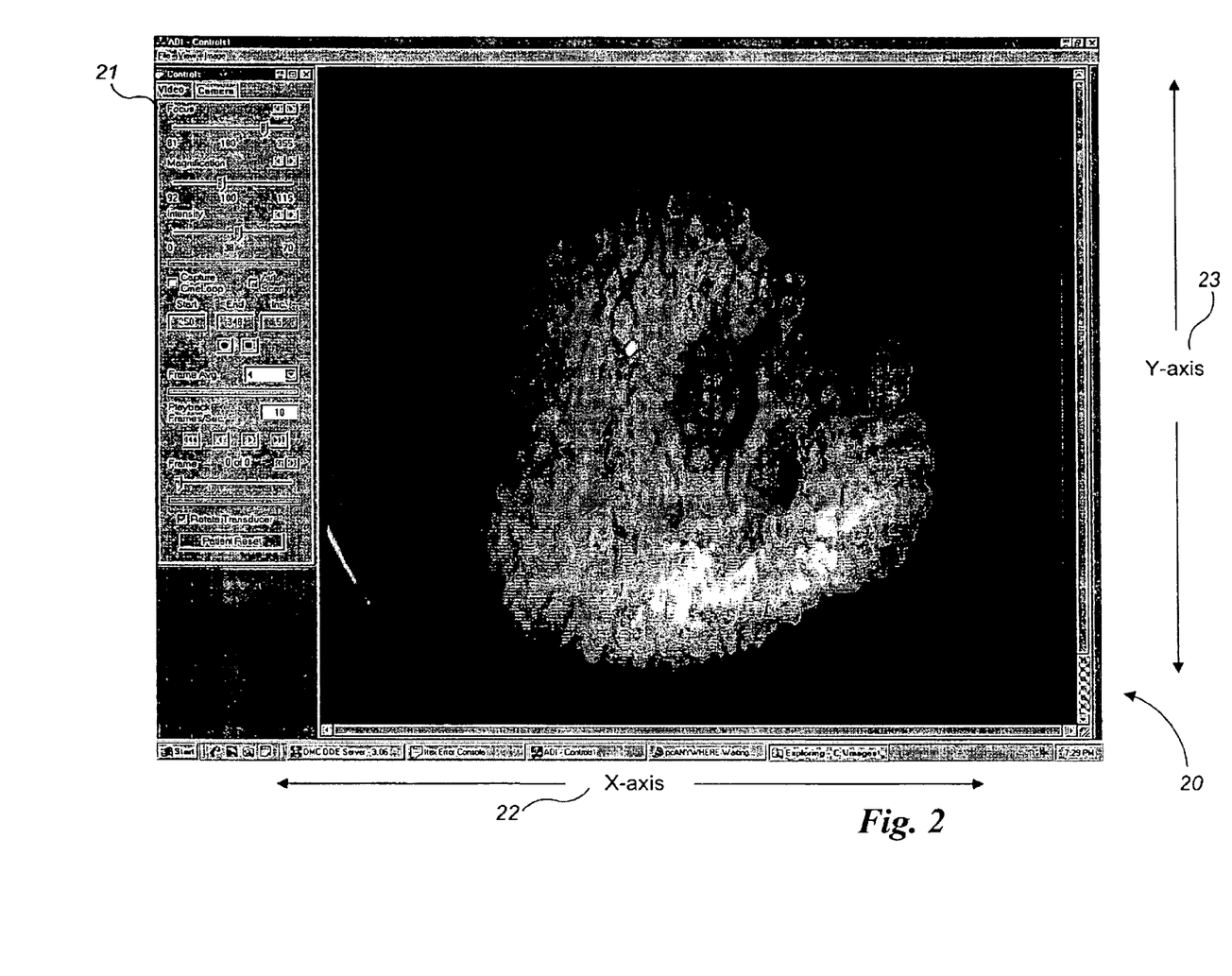
FIG. 2 is an illustration and picture showing the operator interface for Biopsy.

FIG. 1 illustrates the imaging of points of interest in the focal plane 2, which is imaged by a video camera 14, or other similar device, and viewed by the operator on a display 20. The location of any detected lesion can be readily determined in two dimensions (e.g., an X coordinate and a Y coordinate), as illustrated in FIG. 2, because the image plane 22 is projected into the detector 6 and viewed by the operator on the display 20. In addition, the controls of this imaging process can readily determine the location of the focal plane 2 (e.g. a Z coordinate) where the coordinates are taken from a fixed reference point marked on the system. For example, the reference point can be that position of the holder of the anatomy (e.g., compression plate holding the breast tissue) closest to the detector, referenced as Z=0.

Figure 3A:
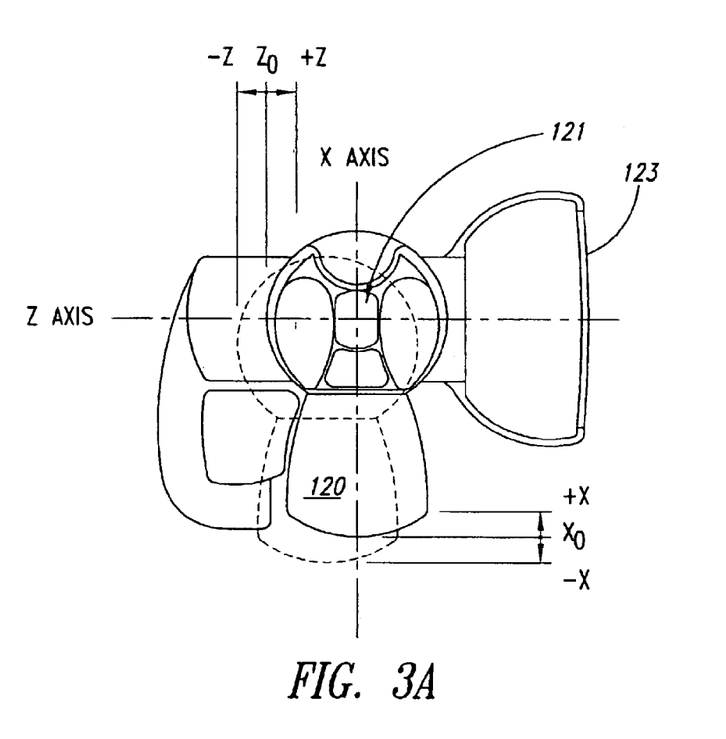
FIGS. 3A–3B illustrate the patient table and handling for biopsy operation.
Figure 3B:
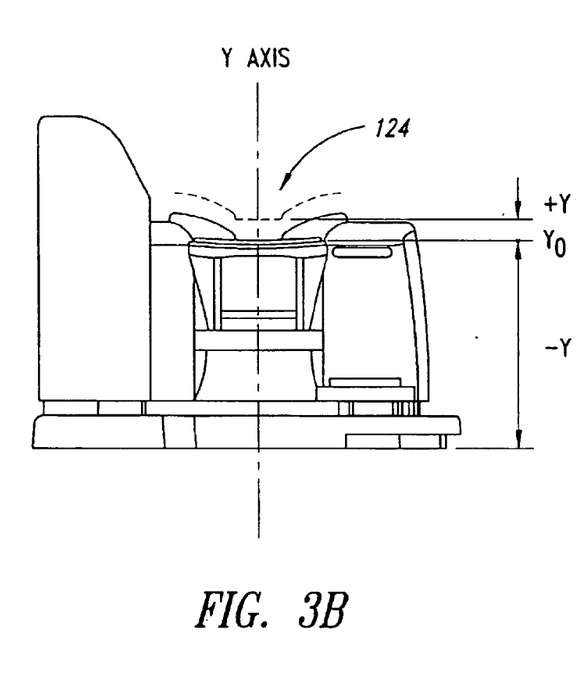

To position any lesion or body part of interest, the imaging system, one configuration of which is shown in FIGS. 3A–3B, can reposition a patient table 120 and thus the lesion or body part of interest, to a preferred position within the field of view of the image. FIG. 3A is a top plan view of the imaging system and illustrates the ability to move the patient and thus, the imaged body part in the X and Z directions. FIG. 3B is a side elevational view of the imaging system and illustrates the ability to move the patient and thus, the imaged body part in the Y direction. The part of the anatomy being imaged is inserted through an opening 121 while the patient is supported on the patient table 120. Further details of the imaging process are provided below.

In a typical ultrasound imaging system, the ultrasonic transducer, ultrasonic detector, and anatomy to be imaged are all placed within a tank containing ultrasonically transmissive fluid, such as water. However, such an approach does not lend itself to the use of ultrasound imaging for guiding a biopsy device. Performing the biopsy with the image tissue immersed in the ultrasonically transmissive fluid may lead to increased infection. However, it is known that ultrasonic signals do not propagate well in air. Thus, draining the ultrasonically transmissive fluid from the tank prohibits proper imaging. Thus, the conventional ultrasonic imaging system cannot be readily used to guide a biopsy probe.

Figure 4:
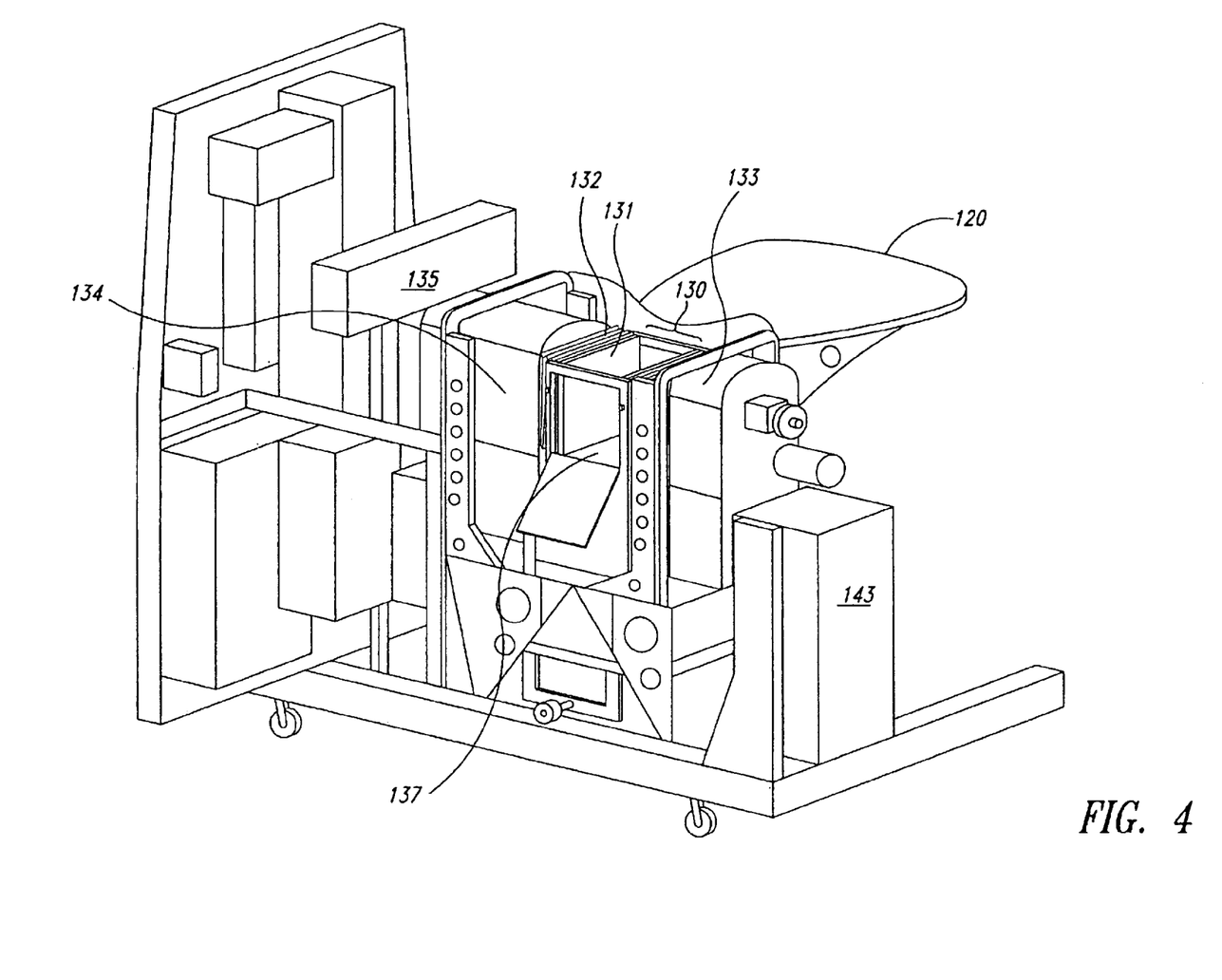
FIG. 4 is an illustration of the interior details of the embodiment on the imaging system and the third imaging chamber used in biopsy.

To overcome this shortcoming, the imaging system of the present invention contains three independently fluid sealed chambers or tanks as illustrated in FIG. 4. A first chamber 133 has a fixed wall on one end and fixed side walls. However, the first chamber 133 has a movable endwall 131, which is coupled to the side walls by a bellows 132, as seen in FIGS. 5–8. The movable end wall 131 is referred to as a compression plate, which retains the patient anatomy in position during imaging and biopsy.

Similarly, a second chamber 134 has a fixed wall on one end and fixed sidewalls. The second chamber 134 also has a movable endwall 131 in opposition to the endwall 131 of the first chamber 133. The movable endwall 131 is coupled to the sidewalls of the second chamber 134 by a bellows 132. As will be described in greater detail below, the movable endwalls 131 (i.e., compression plates) also form endwalls of a third chamber 130. The portion of patient anatomy to be imaged in placed through the opening 121 (see FIG. 3A) and into the third chamber 130.

The first, second, and third chambers 133, 134, and 1304 respectively, are all filled with a selected ultrasonically transmissive liquid. In an exemplary embodiment water is used as the selected ultrasonically transmissive fluid.

Once the patient anatomy is positioned within the interior portion of the third chamber 130, the two compression plates 131 are moved toward each other to retain the patient anatomy in a desired position during the imaging process and during a biopsy procedure. It should be noted that the present invention can be implemented with a single movable compression plate 131 with the opposing compression plate 131 being fixed in position. In this manner, only a single compression plate is movable and is moved toward the fixed compression plate to retain the anatomy in position during imaging and during the biopsy procedure. In addition, other devices may be used to retain the patient anatomy in the desired location during the imaging process and the biopsy procedure.

In an exemplary embodiment, the ultrasonic transducer 1 (see FIG. 1) is positioned in the first chamber 133 and immersed in the ultrasonically transmissive liquid. At least a portion of the ultrasonic detector is positioned within the second chamber 134 and submersed in the ultrasonically transmissive liquid. The portions of the ultrasonic detector positioned within the second chamber 134 would typically include the lens system 3 (see FIG. 1), the ultrasound reflector 5, and a bottom portion of the ultrasound hologram detector 7.

In operation, ultrasound signals (i.e., the plane wave 1a) are generated by the transducer 1 and transmitted through the ultrasonically transmissive liquid in the first chamber 133 and coupled to the third chamber 130 via the compression plate 131. The ultrasonic wave passes through the portion of patient anatomy inserted in the third chamber 130 and passes through the opposing compression plate 131 and into the second chamber 134. The ultrasonic signal in the second chamber 134 is focused by the lens system and detected in a conventional manner, such as that described above. The advantage of the multi-chambered system of the present invention is that the third chamber 130 is isolated from the ultrasonic transducer 1 and the ultrasonic detector in the first and second chambers 130 and 134, respectively. As will be described in greater detail below, this isolation permits the draining of the ultrasonically transmissive fluid from the third chamber 130 and permits access to the imaged portion of the patient anatomy for a biopsy procedure.

The multi-chambered approach of the present invention allow ready access to the patient anatomy, but introduces two additional objects, namely the compression plates 131, which attenuate the ultrasound signal.

These compression plates 131 are selected to be of material that passes ultrasound with minimum attenuation and at the same time has a low reflection of ultrasound as the ultrasound passes from a coupling liquid (e.g., water) into the compression plate 131 and subsequently as it passes from the movable end wall back into the coupling liquid. In other words, the acoustical impedance of the material composing the compression plates 131 is to be as close as possible to the acoustical impedance of water. The acoustical impedance of the compression plates 131 is given in equation (1) below:

$$z(m)=\sigma(m)*v(m) \quad (1)$$

where $\sigma(m)$ is the density of the material of the compression plates and $v(m)$ is velocity of ultrasound in the material of the compression plates.

The acoustical impedance of water or other similar coupling fluid is characterized by the following:

$$z(w)=\sigma(w)*v(w) \quad (2)$$

where $\sigma(w)$ is the density of water or other coupling fluid and $v(w)$ is the velocity of water or other coupling fluid.

The selection of material for the compression plates 131 (i.e., the movable end walls) is selected to provide minimum reflectivity of the ultrasound signal. Reflectivity is given by the following:

$$r(m-w) = \frac{z(m)-z(w)}{z(m)+z(w)} \quad (3)$$

where r is the reflectivity and all other terms have been previously defined.

In an exemplary embodiment, it is desired to reduce the reflectivity to less than 1. Since the square of the reflectivity represents the energy reflected, a reflectivity of 1 equates to 1% energy reflection. Thus, to achieve less than 1% energy reflection, $z(m)$ must be between $1.0*z(w)$ and $1.22*z(w)$. Such design criteria can be achieved by materials, such as a cross-linked polystyrene. A particularly useful material is sold by the trade name TPX.

Figure 5:
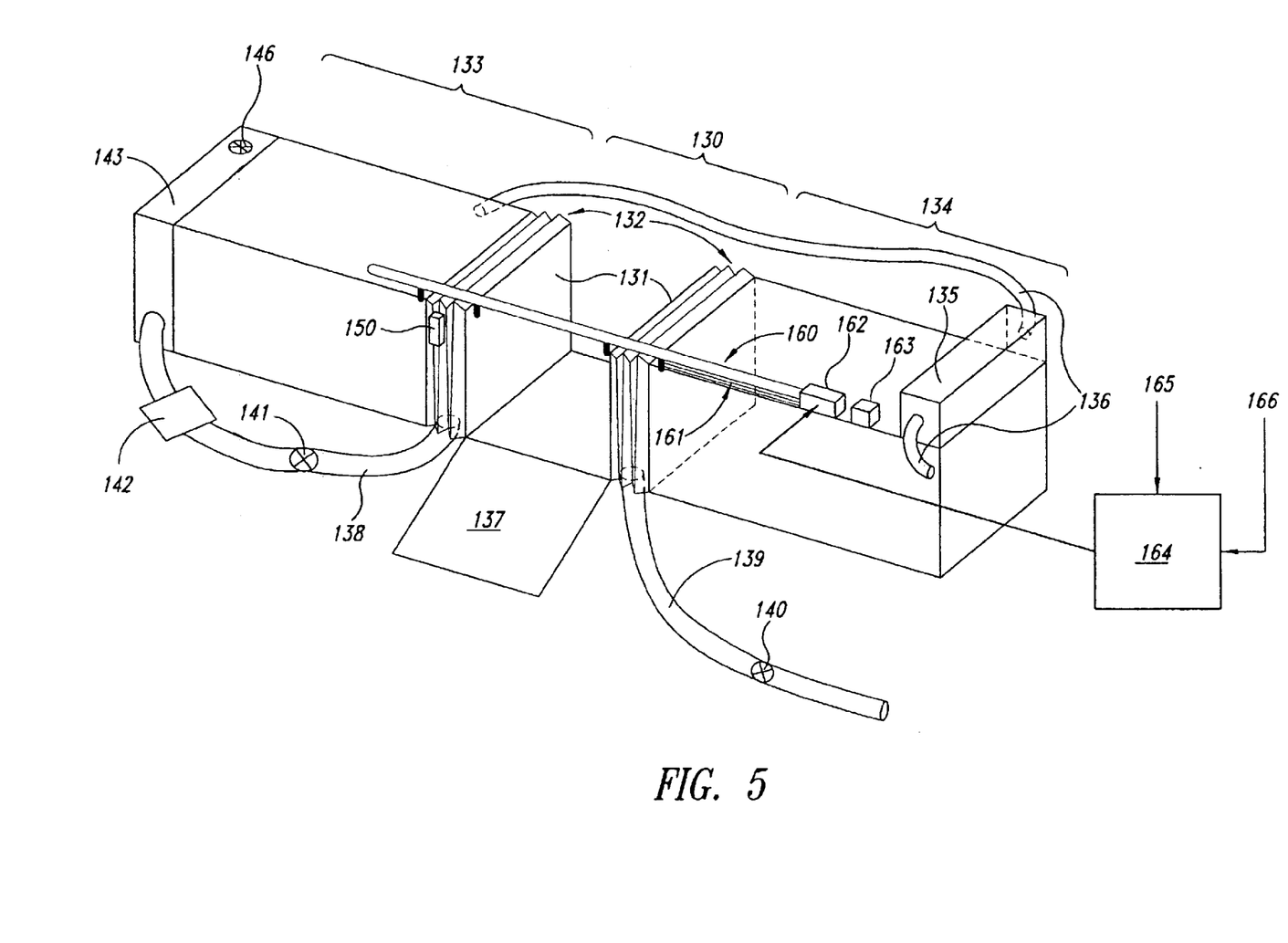
FIG. 5 is an illustration of the interior details of the third chamber imaging tank useful in performing biopsy.

The compression plates 131 are movably attached to a rail 160, as shown in FIG. 5, and attached to a drive mechanism 161 which is driven by drive motors 162. These are in turn controlled by a motor controller 164 that is activated by an operator input controls 165 or the patient input controls 166. The compression plates 131 provide acoustical coupling to the breast while the breast or other body part is compressed within the compression plates 131. The compression serves the function of providing near equal thickness to the breast in the field of view and allows the system to maintain acoustical coupling and thus imaging during the biopsy procedure. Safety overrides 162 prevent physical harm or damage to the breast be or body part being imaged by limiting the pressure applied to the compression plates 131.

It is apparent to those skilled in the art that an acoustical coupling must be provided from the transducer 1 of FIG. 1 to the detector 6. For practical applications, the acoustic energy most commonly will be at frequencies above 1 MHz (one million cycles per second). It also is known to those skilled in the art that at these frequencies, the ultrasound cannot be coupled efficiently through air. A common means of coupling such sound is by the use of a liquid (e.g., water) or other known fluids commonly known to couple sound. Thus, it is apparent that all of the full cross-section of the sound wave must have fluid to pass through to the body part being imaged as any air would severely attenuate the ultrasound being used.

In the configuration of this invention, the imaging chain (from source transducer to detector) passes through the three separately sealed chambers 130, 133, and 134. Thus, a means must be provided to keep all three chambers full of water or other imaging fluid during the imaging process. As the compression plates 131 move together, the volume of the first chamber 133 and the second chamber 134 increases and the volume of the third chamber 130, decreases by a volume that matches the increase in the volume of the first and second chambers. In a like manner, when the compression plates 131 are decompressed or opened, the volumes of the first and second chambers 133 and 134 decrease while the volume of the third chamber 130 increases by a volume that matches the total decrease in the volumes of the first and second chambers.

One feature of this invention is the incorporating of a vented fluid make up tank, 135 which is fluid communication with the first and second chambers 133 and 134 via passages 136, such as an open hose or tube. With the compression plates 131 at maximum compression (i.e., the third chamber 130 is at minimum volume), sufficient fluid is placed in the first and second chambers 133 and 134 and the hoses 136 in FIG. 5 such that the fluid level is at the bottom of the make up tank 135. Note, the make up tank 135 is placed at a higher elevation than the top of the first and second chambers 133 and 134. As the compression plates 151 are opened, the volume of both the first chamber 133 and the second chamber 134 decreases and the water or other imaging fluid in these chambers is forced up through the passage 136 into the make up tank 135. The volume of the make up tank 135 is selected to be of such capacity that all of the fluid displaced by the widening compression plates 131 can be contained in this make up tank 135 without overflowing. Typically the volume of the make up tank 135 is approximately 2 gallons. Thus, the make up tank 135 and the first and second chambers 133 and 134 compromise a supply system that maintains the fluid levels in the first and second chambers irrespective of the position or movement of the compression plates 131.

There are several features to note in the third chamber 130, which is illustrated in FIG. 5 separated from the first and second chambers 133 and 134. The third chamber 130 has six walls (i.e., a top wall, bottom wall, two sidewalls, and two endwalls). As previously discussed, the two endwalls are provided by the compression plates 131, which are in the imaging pathway (i.e., in the pathway of the ultrasound signal). The compression plates 131 are coupled to the side walls of the first and second chambers 133 and 134 by the respective bellows 132. It is noted that the third chamber 130 can be drained by means of a hose 139 and an in-line valve 140 to drain the fluid to a city drain or other disposal means. It is further noted that the third chamber 130 can be filled from an imaging fluid tank 143 by means of a connecting hose 138 with an in-line valve 141 shown in FIG. 5.

Figure 6:
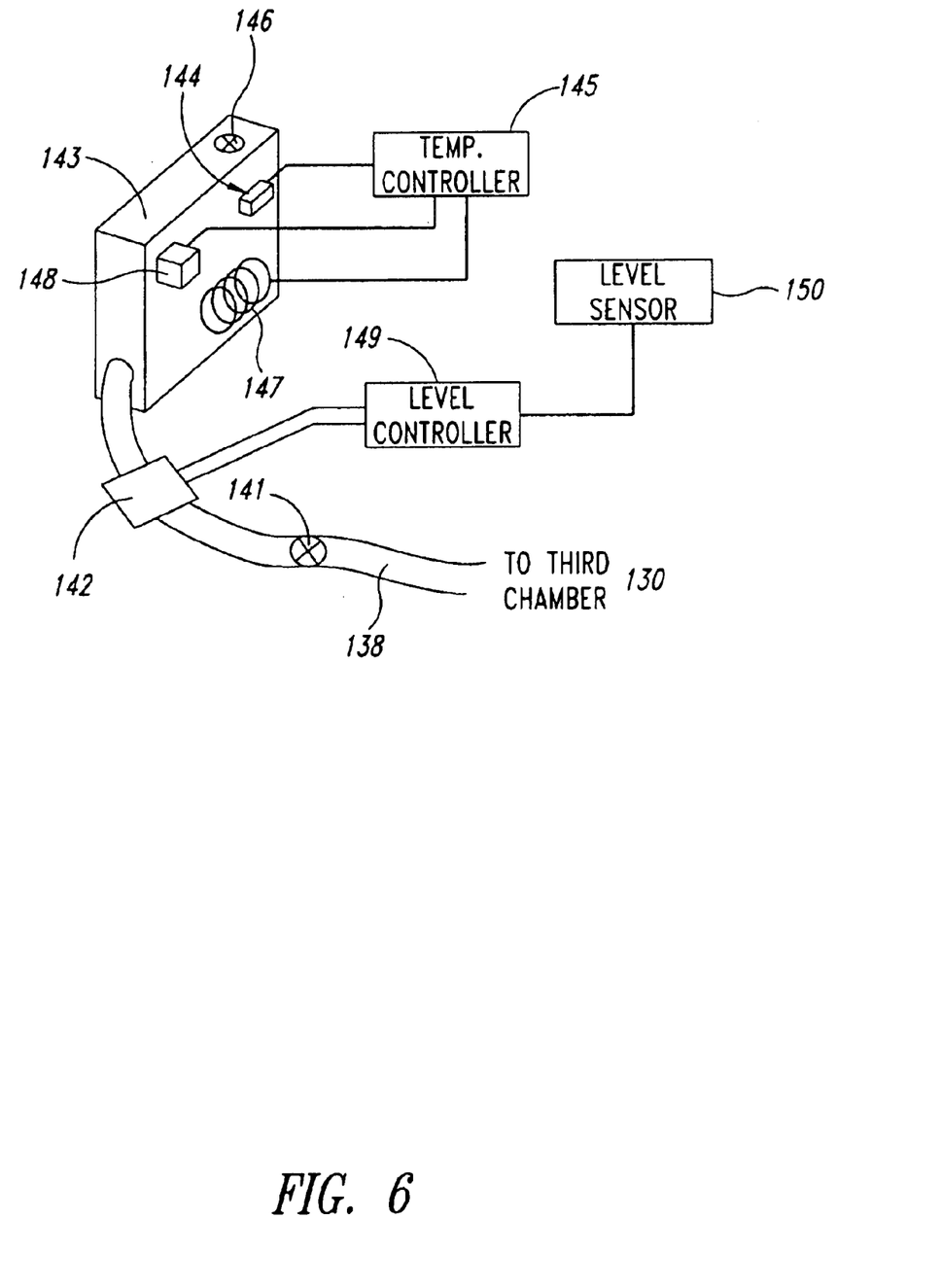
FIG. 6 is an illustration of the imaging fluid make-up system for the third chamber imaging tank.

FIG. 6 illustrates the features of the imaging fluid tank 143. The imaging fluid tank 143 is connected to the third chamber 130 by means of the open hose 138 and valve 141. When the operator elects to fill the third imaging chamber 130, valve 141 is opened. The fluid level in the third chamber 130 is sensed by a level sensor 150, which provides a signal to a level controller 149, which, in turn, provides a control signal to a pump 142. In an alternative embodiment, the level controller 149 also provides a control signal to the valve 141 to automatically open and close the valve. A vent 146 equalizes pressure within the imaging fluid tank 143 to prevent the creation of a vacuum or the buildup of pressure that would otherwise prevent the pump 142 from operating properly. As the fluid reaches the desired level (e.g., at the top of the compression plates 131), the level sensor 150 provides the signal to stop the pump 142 and close the valve 141. Closure of the valve 141 prevents backflow of fluid from the third chamber 130 into the imaging fluid tank 143. Thus, water level within the third chamber is automatically controlled by the system of the present invention.

To insure that the imaging fluid placed in the third chamber 130 is at or near body temperature, a temperature sensor 144 in the imaging fluid tank 143 monitors fluid temperature. As the temperature is below the desired preset value, the temperature sensor 144 provides a signal to a temperature controller 145. In am exemplary embodiment, the temperature controller 145 is a simple On-Off controller. When activated by the temperature sensor 144, the temperature controller 145 supplies power to a heater coil 147 within the tank. One skilled in the art will recognize that temperature control system described above may be a standard thermocouple controlled heater system. A recirculating pump 148 is inserted in the imaging fluid tank 143 to circulate the fluid therein. The circulation of the fluid assists in maintaining uniform temperature of the ultrasonically transmissive fluid contained within the imaging fluid tank 143.

Figure 7:
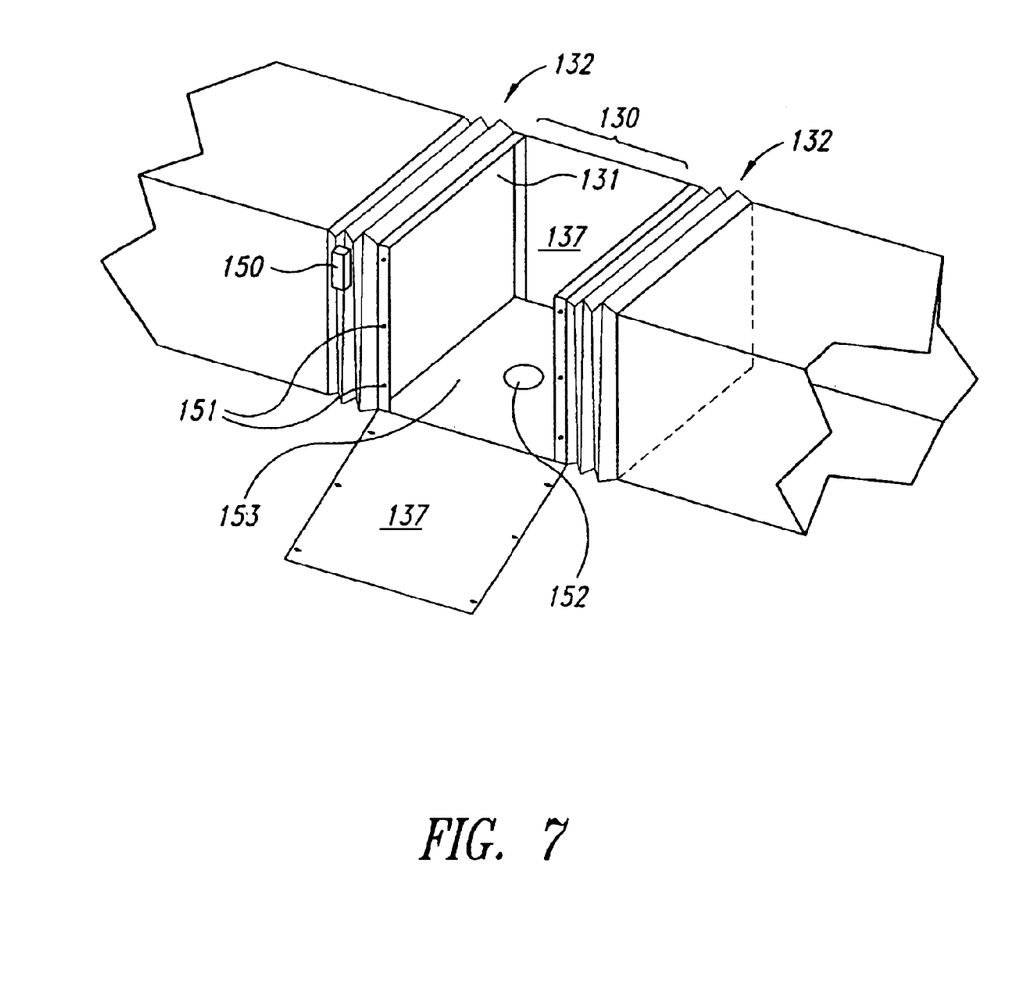
FIG. 7 is an illustration of the door access to the third chamber imaging tank.

Additional features of the third chamber 130 are illustrated in FIG. 7. The two sidewalls of the third chamber 130 are provided in the form of access panels 137, which are each optically transparent and removable by means of two twist lock fasteners 151. Other types of fasteners may be used in place of the twist lock fasteners 151 to provide ready access to the interior portion of the third chamber 130. Those skilled in the art can appreciate that the access panels 137 must provide a watertight seal when in the closed position to prevent leakage of the ultrasonically transmissive fluid from the third chamber 130. The seal may be provided by a number of known techniques, which need not be described herein.

When opened, one or both of the access panels 137 fold down by means of a hinge (not shown) to a position shown in FIGS. 5 and 7. The access panels 137 allow convenient access to the breast or body part being imaged. Such access is essential in the biopsy procedure. With this access the doctor or operator may sterilize the breast or body part at the point of entry of the guided biopsy needle.

FIG. 7 also illustrates a light 152 placed below the third chamber 130 to illuminate the breast or body part being imaged. In this embodiment, a floor panel 153 of the third chamber 130 is made from an optically transparent material. The light 152, which may be a low voltage light, provides illumination of the breast or body part through the floor panel 153. Because the access panels 137 are also transparent, the doctor or operator can observe the breast or body part being imaged. When the transparent imaging fluid is drained from the third chamber 130 and one or more of the access panels 137 are opened, the light 152 provides illumination through the floor panel 153 of the third chamber. Similarly, when the access panels 137 are closed and the third imaging chamber 130 is filled with transparent imaging fluid (e.g., water), illumination of the breast or body part being imaged is provided by the light 152 as well as ambient light which may enter the interior of the liquid filled third chamber 130 via the transparent access panels 137.

Figure 8:
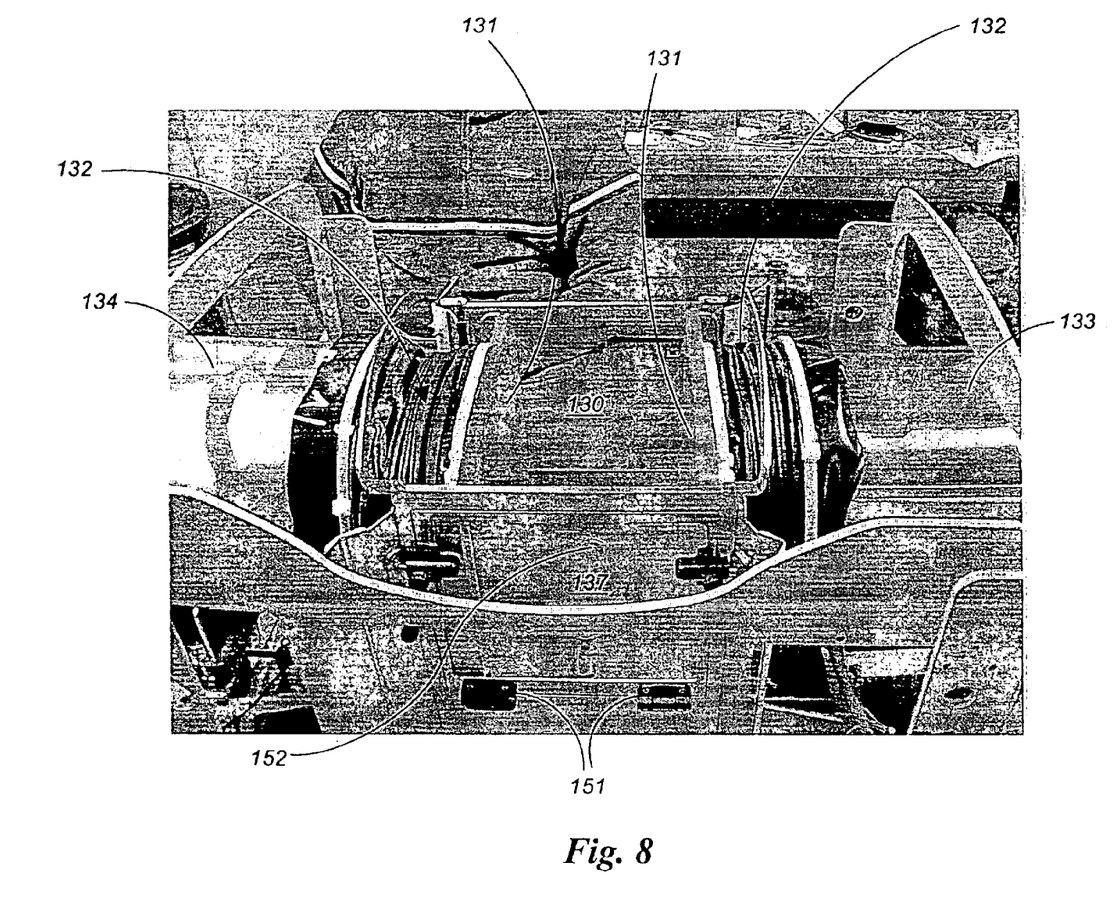
FIG. 8 is a picture showing the construction of the third chamber imaging tank.

The third chamber 130, compression plates 131, bellows 132 together with the access panels 137 and fasteners 151 are shown in the photograph of FIG. 8.

The invention described above provides the operator with a guided biopsy system utilizing three-dimensional position information of the lesion's location. The system provides guidance to make the initial incision and start the needle approach. Thereafter, real-time image guidance is provided in this invention. The biopsy guidance system helps ensure an accurate approach to the breast lesion.

The lesion is located during an ultrasonic imaging procedure, such as described above. For biopsy, water is drained from around the breast to create a more sterile environment for the incision and needle insertion processes. The removal of water around the breast reduces ultrasonic coupling around the skin and periphery of the breast, causing loss of image information in these areas. As noted above, the patient may be repositioned until the lesion is moved toward the center of the image. Proper repositioning of the lesion helps assure adequate ultrasonic coupling in the vicinity of the lesion even after the ultrasonically transmissive fluid has been drained from the third chamber 130. Since the needle must be inserted into the breast for a short distance before being seen on the imaging display, ability to pre-position and manually advance the needle along a known path is critical. The present invention provides a technique using the knowledge of lesion's location in the three-dimensional space to provide an accurate biopsy guidance and implementation system.

The biopsy guidance system can be deployed only during biopsy localization procedures. During system use other than biopsy, the biopsy guidance system is stowed so as not to interfere with standard imaging procedures.

The present invention is generally applicable to the location of a lesion or biological structure from which a biopsy sample will be taken and to the guidance of a biopsy device to obtain the biopsy sample. In certain examples presented herein, breast tissue is imaged and biopsy samples obtained. However, those skilled in the art will appreciate that the imaging and biopsy guidance system of the present invention is generally applicable to other portions of the anatomy and thus is not limited solely to breast imaging and breast lesion biopsy guidance. The biopsy procedure is conducted while breast is under compression and after water has been drained from the patient tank. Biopsies are generally conducted perpendicular to sound path and parallel to an X-Y plane at a designated Z-axis location. Biopsy access is provided from both the cranial (top of the breast) and caudal (bottom of the breast) sides of the imaging tank.

Image viewing is provided on the display 20 (see FIG. 1) so that physician can readily view images and track needle movement from both sides of patient tank. The operator will note the target lesion on the real-time image, which will provide X and Y location relative to the biopsy device.

The physical position of the ultrasonic lens system 3 (see FIG. 2) is calibrated so that a correspondence exists with physical focal plane location. That is, when the lesion is in focus, the focal plane 2 will correspond to a specific Z location. The biopsy guidance system can locate focal plane 2 to within +/−1 mm of associated lens setting.

Figure 9:
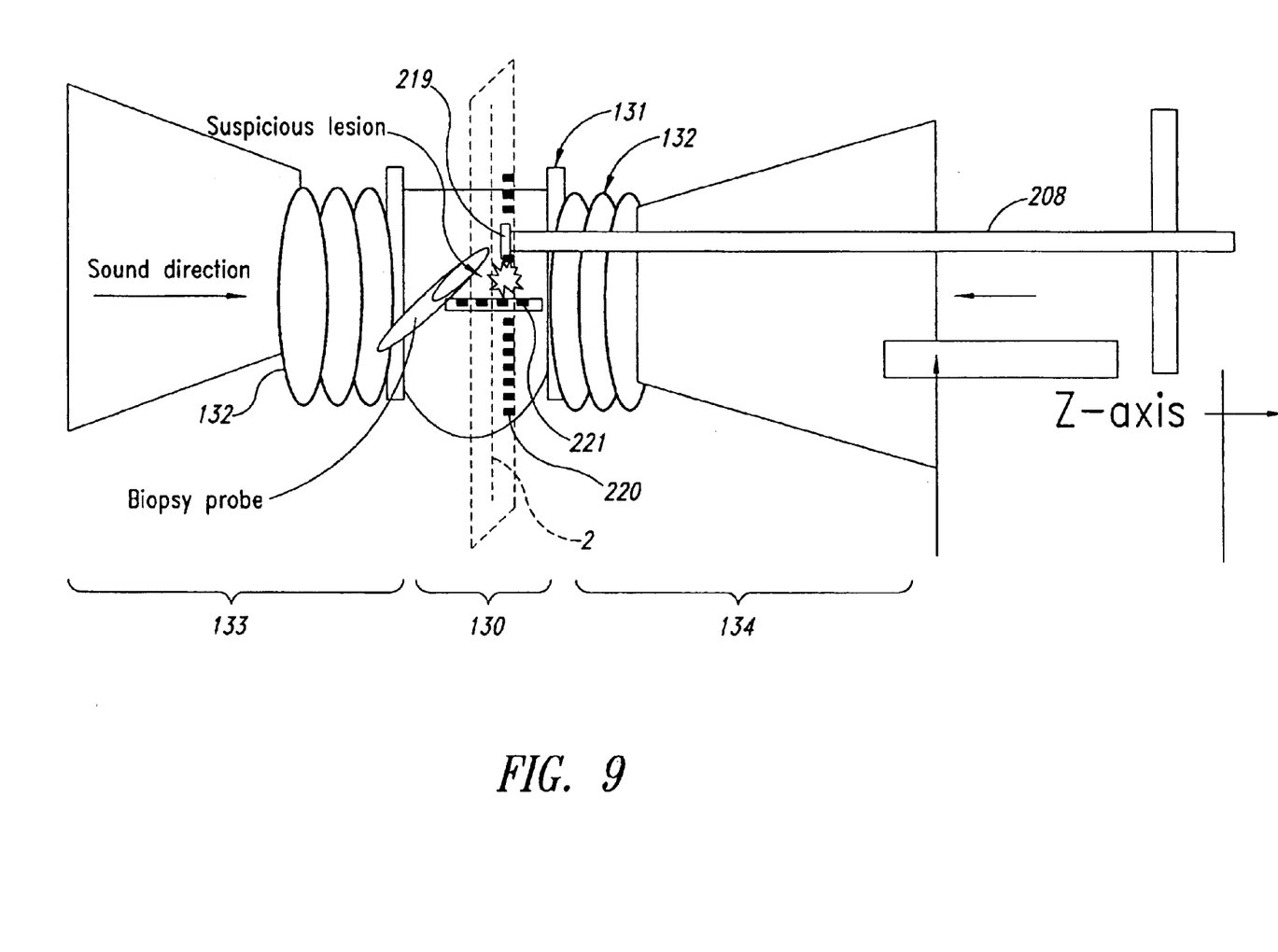
FIG. 9 is an illustration of the biopsy guidance system.

This invention contains the apparatus and method for performing a biopsy by using the provisions of the patient handling system of FIGS. 3A–3B and the multi-chamber imaging tank of FIGS. 5–8. FIG. 9 illustrates a technique by which the system of the present invention may be used to guide a surgeon on the positioning of a biopsy device. As shown in FIG. 9, a suspicious lesion has been identified in the breast. As previously discussed with respect to FIGS. 3A–3B, the breast may be repositioned so as to move the suspicious lesion to a more centrally located position in the display 20. For example, FIG. 2 illustrates a suspicious lesion which has been positioned to approximately the center of the display 20. The X and Y coordinates along the X-axis 22 and the Y-axis 23 and may be numerically displayed on the GUI 21 of the display 20.

As shown in FIG. 9, a biopsy guide member 208 is positioned along an exterior portion of three chambers 130, 133 and 134. The guide member 208 may be a round metal rod or other solid structure that is scaled in mm increments. The guide member 208 is initially positioned in a fixed relationship with respect to a reference point in the Z direction (i.e., the direction of propagation of the ultrasound waves). For example, the guide member 208 may be positioned with reference to the compression plate 131 located closest to the ultrasound detector (e.g., Z=0). The lens system 3 is adjusted to image the lesion of interest in the focal plane 2. As the lens system 3 is adjusted and the focal plane 2 positioned at the desired location coinciding with the lesion of interest, the variation in the Z-axis from the reference point (i.e., Z=0) can be readily determined.

Once the final location of the lesion of interest has been determined in the Z direction, the guide member 208 may be mechanically manipulated, using the one millimeter guide marks, to coincide with the position of the focal plane 2. In this manner, the physician or operator can readily determine the plane in which the lesion of interest is located.

A light source 219 is positioned at a terminal end of the guide member 208 that will indicate the location of the focal plane 2 on the external anatomy of the patient. In an exemplary embodiment, the light source 219 is designed to generate light in the form of a narrow plane 220 that is along the Y-axis and perpendicular to the Z-axis. This provides an external indicator to the physician or operator the plane in which the lesion of interest is located.

The guide member 208 is also adjustable in the Y direction. Using marks, such as one millimeter marks, the guide member 208 may be manipulated in the Y direction to coincide with the Y coordinate of the lesion.

The light source 219 also generates light in the form of a narrow plane 221, which is in the Z direction and orthogonal to the Y direction. Thus, the light source 219 emits light in the form of two narrow planes 220 and 221 to form a cross-haired indicator whose intersection coincides with the Y and Z coordinates of the lesion. This external marking of the patient anatomy provides an accurate point of entry for the biopsy probe. The accurate point of entry, combined with the real-time imaging on the display 20, allows the physician or operator to easily manipulate the biopsy probe and obtain a sample of the lesion.

Figure 10:
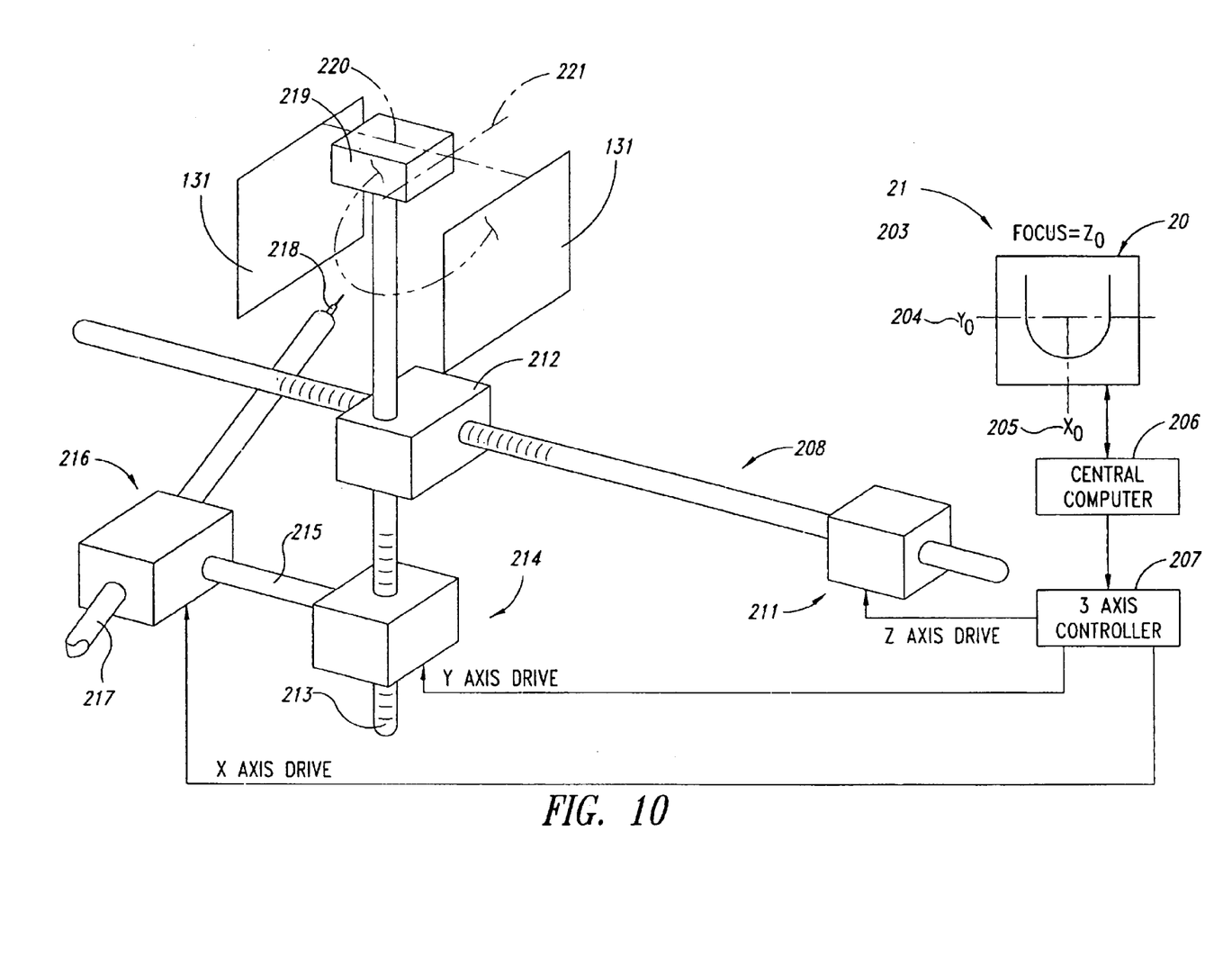
FIG. 10 is a functional diagram illustrating the positioning of the needle for biopsy.

In an alternative embodiment, the system may automatically guide a biopsy probe to the location of the lesion. This embodiment is illustrated in FIG. 10 where a central computer 206 controls a 3-axis controller 207. The 3-axis controller 207 in turn generates control signals for a Z-axis drive 211, a Y-axis drive 214 and a Z-axis drive 216. In an exemplary embodiment, the Z-axis drive 211, Y-axis drive 214 and X-axis drive 216 may be implemented using stepper motors. In this embodiment, the 3-axis controller 207 is a stepper motor controller. In this embodiment, the guide member 208 is coupled to the Z-axis drive for movement in the Z direction. That is, the Z axis drive 211 is moved back and forth in the Z direction. A mounting fixture 212 is fixedly coupled to the guide member 208 for movement therewith. The Y-axis drive 214 is also coupled to the mounting fixture via a vertical guide member 213. The vertical guide member 213 is fixedly coupled to the mounting fixture 212 such that the Y axis drive 214 moves back and forth in the Y direction under control of the 3-axis control 207. The Y-axis drive is positioned by the 3-axis controller 207 to a location coinciding with the Y location of the lesion. A mounting fixture 215 is fixedly coupled to the Y axis drive 214 and moves therewith. The X-axis drive 216 is fixedly coupled to the mounting fixture 215 such that it also moves back and forth in the Y direction.

A horizontal guide member 217 is movably coupled to the Z-axis drive 216. The horizontal guide member 217 moves back and forth in the X direction under control of the X-axis drive 216. A biopsy needle holder fixture 218 is coupled to a terminal end of the horizontal guide member 217 for insertion into the breast. Thus, the biopsy needle, which is attached to the biopsy needle holder fixture 218 is movable in three dimensions. Movement in the Y and Z directions are performed under control of the 3-axis controller 207 before any contact is made with the patient. Once the needle biopsy holder fixture 218 is positioned at the proper Y and Z coordinates, the X-axis drive may be activated to insert the biopsy needle into the breast and position the biopsy needle at the appropriate X coordinate. Thus, in one embodiment, the system provides the appropriate X, Y and Z coordinates to automatically obtain a biopsy sample.

FIG. 10 illustrates a particular embodiment of an automated biopsy system. However, those skilled in the art will recognize that alternatives may be used to implement an automated biopsy system. For example, the three drive motors discussed above may be replaced by a robotic device, such as is known in the art. Alternatively, the system may provide automatic positioning in less than three dimensions. For example, the system may automatically position the biopsy needle holder fixture 218 at the appropriate Y and Z coordinates. In this embodiment, the X-axis drive 216 is manually operated under control of the physician or operator using the imaging on the display 20 to guide the biopsy needle in the X direction. The present invention is not limited by the specific implementation of the automated biopsy system.

In operation, the operator will set cursors on the lesion of interest, which will determine the values of Y(o) 204 and X(o) 205. The Y(o) position information is fed to the central computer 206 which in turn sends a signal to the 3-axis controller 207 and which in turn, drives the Y-axis drive 214.

The operator selects the focal plane 2 by either a fixed protocol of screening or manually adjusting the lens system 3 (see FIG. 1) as the operator observes the images on the display 20. This process results in a determination of the focal plane 2, which corresponds to a specific location in the Z direction. The coordinates of the focal plane 2 in the Z direction are displayed on the display 20 and may be recorded by the central computer 206. The Z-axis position information is sent to the Z-axis drive 211 via the 3-axis controller 207 to position the movable mounting fixture 212 to the proper position.

In this embodiment, the light fixture 219 may generate a light in the form of the narrow plane 220 to provide an indication of the focal plane 2 on the external anatomy of the patient. A separate light fixture (now shown) may be coupled to the Y-axis drive 214 or vertical guide member 213 to generate the narrow plane of light 221 to indicate the Y plane of the lesion.

Attached to the Y-axis drive 214 is the X-axis motor 216. In a similar manner to the operation of the Y positioning fixture, the X-axis drive 216 will receive the X(o) position signal via the central computer 206 and the 3-axis controller 207 to drive the biopsy needle holder fixture 218 inward in automatic operations or remain stationary to allow the needle to be advanced manually in manual operation. It is noted that at all times the needle's path and progress will be visible on the display.

The location of focal plane 2 can be displayed as a numerical focus position on a graphical user interface (GUI) 21 (see FIG. 2) using the display 20. Distances are computed from the focal plane location to the compression plates to ensure at least 4 mm clearance for needle firing. A warning will be displayed when this distance is equal to or less than 4 mm.

After the lesion is in focus, the system can locate the focal plane of the lesion physically by displaying a temporary marker of that focal plane location and hence the Z coordinate on the patient's skin (e.g., laser pointer that fans out to project a line indicating the focal plane of the lesion). The biopsy guidance system attaches to the imaging system of this invention via a rail (e.g., rail attached to the internal frame holding the patient tank) and will provide translation of the biopsy guidance system in the Z, X, and Y, directions.

Whether the system is operated in a manual mode, as discussed with respect to FIG. 9 or in an automated mode as discussed with respect to FIG. 10, the various guide members may be locked in position once the proper coordinates have been located. For example, in the manual mode, the terminal end of the guide member 208 may be locked in position in the Y- and Z-axes. Once locked, the biopsy guidance system maintains the position of the "pointer" to within +/−0.01". In one embodiment, the biopsy needle is manually positioned and advanced using the projection on the skin for guidance. For operation in the automated mode, the biopsy needle holder fixture 218 may be positioned to the appropriate location in the Y and Z dimensions and the system locked to reduce vibrations. The X-axis drive 216 may be activated automatically under control of the central computer 206 or may be manually advanced by the physician or operator using the image of the display 20 to guide the biopsy needle.

At system startup software initializes the motion control, the lens system 3 and compression plates 131 to a home position. Calibration data is logged for relationship between acoustic lens positions and focal plane location, and location of compression plates 131. Software computes Z-axis location via acoustic lens position. The software computes the distance between focal plane 2 and compression plates 131 and issues warning if plate is within 4 mm of the lesion.

The Process of Performing a Biopsy

Perhaps one important way to describe the features of this invention is to outline the procedure of performing a biopsy utilizing the features of this invention.

Sterilizing the Third Imaging Chamber

With one or more of the access panels 137 of the third chamber 130 opened and the valve 141 (see FIG. 5) on the fill line in the closed position and the drain line valve 140 being closed, the third chamber 130 can be cleaned and sterilized.

Filling the Third Imaging Chamber

The valve 140 in the drain line is closed.

The access panels 137 are closed upward and secured to a liquid tight seal by the fastener 151.

The valve 141 is opened and the level sensor 150 sends a signal to the level controller 149 and the fill pump 142. The fill pump 142 fills the third chamber 130 to the desired level and valve 141 is closed. Note the imaging fluid is preconditioned by the recirculating pump 148 of FIG. 6, temperature monitor 144 and heater 147 in the imaging fluid tank 143.

Placing the Patient and Anatomy to be Imaged

The patient is positioned on the patient table 120 of FIG. 3 and either the right or left breast is positioned in the opening 121.

Water or imaging fluid that is displaced from the third chamber 130 runs over a level control internal spillway to be disposed.

Imaging the Patient

The imaging system is turned on and the breast or other body part is imaged with the display showing the image as illustrated as the operator interface for biopsy in FIG. 2.

A lesion of interest is noted by the operator and confirmed by the doctor.

Repositioning the Patient

The operator moves the patient table 120, thus the patient and the anatomy of interest to reposition the lesion of interest to the preferred location (e.g., generally in the center of the field of view). With the compression plates 131 attached to the patient table, this repositioning may be accomplished with the image remaining on the operator interface during repositioning.

The operator notes the Z-axis position (i.e., the position of the focal plane 2 shown on the monitor), and establishes the X-axis and Y-axis positions of the lesion by setting the cursors on the operator interface (e.g., the GUI 21).

Preparing for Biopsy

With the patient being imaged remaining in a still state and the breast or other body part being imaged fixed between the compression plates 131 the real time image remains on the display 20.

The operator then opens the drain valve 140 and the water or imaging fluid surrounding the breast or body part drains from the third chamber 130 to city drain but since the compression plates 131 remain in a compressed state the image remains on the display 20. As previously discussed, acoustic coupling is maintained through the third chamber 130 via the compression plates 131 and the patient anatomy. Acoustic coupling in the first and second tanks 133 and 134 occur in a conventional manner, as is known in the art.

When the water of imaging fluid is completely drained from the third chamber 130, the operator loosens the side wall latch 151 (see FIG. 8) and opens one or more of the axis panels 137 to permit the doctor to perform the biopsy. Note the bottom surface of the patient table has a minimum height from the floor (e.g., 42 inches minimum) sufficient to allow the doctor (seated) to comfortably perform the biopsy.

The doctor or operator performs the sterilization of the exposed surface of the breast or other body part being imaged in the region in which the biopsy is to be performed.

Positioning for Biopsy

The biopsy guide member 208 of FIG. 10 is then placed in position along the imaging system. Note the guide member 208 may be permanently attached to the biopsy system, folded out of the way and returned for use by a hinge at the end of the arm or mounted and dismounted to the imaging system.

The signal of the Z-axis position (i.e., the focal plane 2) is sent from the central computer 206 to the controller of the Z-axis drive 211 of the movable mounting fixture. The Z-axis drive 211 positions the movable mounting fixture 212 such that the attached plane indicator light 219 illuminates a line of light on the breast or other body part undergoing biopsy procedure. This line of light indicates the Z-axis plane which would intersect the lesion of interest.

The Y-axis coordinate established by the operator by the setting on the GUI 21 of the display 20 is sent to the central computer 206 which in turn provides the signal to the controller of the Y-axis drive 214 which positions the biopsy needle guide (e.g., the biopsy needle holder fixture 218 of FIG. 10) in the proper Y or vertical dimension. Thus the Z-axis and Y-axis positions are thus established for the biopsy needle guide.

Performing the Biopsy

With the biopsy needle guide being positioned in two coordinates (Z-axis and Y-axis) the only remaining action is to insert the biopsy horizontally in the X direction. This may be accomplished either by the doctor manually inserting the biopsy needle while watching its position on the display 20 or could be accomplished by allowing the X-axis information from the operator interface to be sent to the X-axis drive 216 to automatically insert the biopsy needle.

Since the Z-axis dimension is shown by the light plane indicator and the needle's progress into the anatomy may be monitored in real time, the doctor may perform the biopsy manually by hand held needle insertion.

Also during the biopsy operation the doctor may adjust either the Z-axis position or the Y-axis position to biopsy other regions as desired as he or she watches the progress of the needle to the lesion by observation on the display 20 of FIG. 2.

When the biopsy procedure is finished and the needle is extracted, the incision closed, the compression plates 131 are opened and the patient removed from the patient table 120.

The third chamber 130 may be sterilized and the system is ready for the next patient.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. An ultrasonic imaging apparatus for imaging a portion of patient anatomy using an ultrasonic transducer and an ultrasonic detector, the system comprising:

first and second tanks filled with a selected ultrasonically transmissive fluid, the first tank containing the ultrasonic transducer and the second tank containing at least a portion of the ultrasonic detector;

a third tank positioned intermediate the first and second tanks and adapted to receive the portion of the patient anatomy to be imaged, the third tank being filled with the selected ultrasonically transmissive fluid; and first and second endwalls to define boundaries between the first and third tanks and between the second and third tanks, respectively, the first and second endwalls being made of a material that is ultrasonically transmissive.

2. The system of claim 1 wherein the first and second endwalls are manufactured from cross-linked polystyrene.

3. The system of claim 1 wherein the first and second endwalls are manufactured from TPX.

4. The system of claim 1 wherein the first and second endwalls are manufactured from material having an impedance such that the reflection of ultrasonic signals is no greater than one percent.

5. The system of claim 1 wherein the selected ultrasonically transmissive fluid is water.

6. The system of claim 1, further comprising a visual indicator of the predetermined focal plane to indicate the predetermined focal plane with respect to an external portion of the patient anatomy.

7. The system of claim 1, further comprising a position retention member to maintain the patient anatomy in a stable position during imaging of the selected anatomical feature.

8. An ultrasonic imaging apparatus for imaging a portion of patient anatomy using an ultrasonic transducer and an ultrasonic detector, the system comprising:

first and second tanks filled with a selected ultrasonically transmissive fluid, the first tank containing the ultrasonic transducer and the second tank containing at least a portion of the ultrasonic detector;

a third tank positioned intermediate the first and second tanks and adapted to receive the portion of the patient anatomy to be imaged, the third tank being filled with the selected ultrasonically transmissive fluid, the third tank having first and second opposing sidewalls, the system further comprising an access panel in the first sidewall to permit access to the portion of the patient anatomy to be imaged; and first and second endwalls to define boundaries between the first and third tanks and between the second and third tanks, respectively, the first and second endwalls being made of a material that is ultrasonically transmissive.

9. The system of claim 8, further comprising a drain aperture to drain selected ultrasonically transmissive fluid from the third tank wherein acoustical coupling between the ultrasonic transducer and the ultrasonic detector is maintained via the selected ultrasonically transmissive fluid in the first and second tanks and the portion of the patient anatomy to be imaged.

10. An ultrasonic imaging apparatus for imaging a portion of patient anatomy using an ultrasonic transducer and an ultrasonic detector, the system comprising:

first and second tanks filled with a selected ultrasonically transmissive fluid, the first tank containing the ultrasonic transducer and the second tank containing at least a portion of the ultrasonic detector;

a third tank positioned intermediate the first and second tanks and adapted to receive the portion of the patient anatomy to be imaged, the third tank being filled with the selected ultrasonically transmissive fluid;

first and second endwalls to define boundaries between the first and third tanks and between the second and third tanks, respectively, the first and second endwalls being made of a material that is ultrasonically transmissive; and a fluid holding tank coupled to the third tank to hold a reserve volume of the selected ultrasonically transmissive fluid.

11. The system of claim 10, further comprising a temperature control system to control the temperature of the selected ultrasonically transmissive fluid in the fluid holding tank.

12. An ultrasonic imaging apparatus for imaging a portion of patient anatomy using an ultrasonic transducer and an ultrasonic detector, the system comprising:

first and second tanks filled with a selected ultrasonically transmissive fluid, the first tank containing the ultrasonic transducer and the second tank containing at least a portion of the ultrasonic detector;

a third tank positioned intermediate the first and second tank and adapted to receive the portion of the patient anatomy to be imaged, the third tank being filled with the selected ultrasonically transmissive fluid;

first and second endwalls to define boundaries between the first and third tanks and between the second and third tanks, respectively, the first and second endwalls being made of a material that is ultrasonically transmissive; and at least one of the first and second endwalls being moveable to retain the portion of the patient anatomy to be imaged.

13. The system of claim 12, further comprising a flexible coupling to couple the moveable endwall to its respective tank.

14. The system of claim 12 wherein movement of the moveable endwall causes a change in a volume of fluid contained in its respective tank, the system further comprising a fluid reservoir in fluid communication with the tank coupled to the moveable endwall to maintain a fluid level of the selected ultrasonically transmissive fluid in the tank.

15. An ultrasonic imaging apparatus for imaging a portion of patient anatomy using an ultrasonic transducer and an ultrasonic detector, the system comprising:

first and second tanks filled with a selected ultrasonically transmissive fluid, the first tank containing the ultrasonic transducer and the second tank containing at least a portion of the ultrasonic detector;

a third tank positioned intermediate the first and second tanks and adapted to receive the portion of the patient anatomy to be imaged, the third tank being filled with the selected ultrasonically transmissive fluid;

first and second endwalls to define boundaries between the first and third tanks and between the second and third tanks, respectively, the first and second endwalls being made of a material that is ultrasonically transmissive; and the first and second endwalls being moveable to retain the portion of the patient anatomy to be imaged.

16. The system of claim 15, further comprising a first flexible coupling to couple the first moveable endwall to the first tank and a second flexible coupling to couple the second moveable endwall to the second tank.

17. The system of claim 15, wherein movement of the moveable endwalls causes a change in a volume of fluid contained in the first and second tanks, the system further comprising a fluid reservoir in fluid communication with the first and second tanks to maintain a predetermined fluid level of the selected ultrasonically transmissive fluid in the first and second tanks.

18. An ultrasonic imaging apparatus for imaging a portion of patient anatomy using an ultrasonic transducer and an ultrasonic detector, the system comprising:

first and second tanks filled with a selected ultrasonically transmissive fluid, the first tank containing the ultrasonic transducer and the second tank containing at least a portion of the ultrasonic detector;

a third tank positioned intermediate the first and second tanks and adapted to receive the portion of the patient anatomy to be imaged, the third tank being filled with the selected ultrasonically transmissive fluid;

first and second endwalls to define boundaries between the first and third tanks and between the second and third tanks, respectively, the first and second endwalls being made of a material that is ultrasonically transmissive; and a visual indicator of the selected focal plane to indicate the selected focal plane with respect to an external portion of the patient anatomy.

19. A method of ultrasonic imaging of a portion of patient anatomy using an ultrasonic transducer and an ultrasonic detector, the method comprising:

activating the ultrasonic transducer in a first tank containing the ultrasonic detector to generate ultrasonic signals, the first tank being filled with a selected ultrasonically transmissive fluid;

coupling ultrasonic signals through an ultrasonically transmissive first endwall between the first tank and a second tank, the second tank being positioned intermediate between the first tank and a third tank;

receiving the portion of the patient anatomy to be imaged in the second tank filled with the ultrasonically transmissive fluid;

coupling ultrasonic signals through an ultrasonically transmissive second endwall between the second tank and the third tank; and detecting ultrasonic signals with the ultrasonic detector in the third tank containing the ultrasonic detector, the third tank being filled with the ultrasonically transmissive fluid.

20. The method of claim 19 wherein the first and second endwalls are manufactured from cross-linked polystyrene.

21. The method of claim 19 wherein the first and second endwalls are manufactured from material having an impedance such that the reflection of ultrasonic signals is no greater than one percent.

22. The method of claim 19 wherein the selected ultrasonically transmissive fluid is water.

23. The method of claim 19 wherein the first and second endwalls are moveable, the method further comprising moving the first and second endwalls to retain the portion of the patient anatomy to be imaged.

24. The method of claim 23 wherein movement of the first and second endwalls causes a change in a volume of fluid contained in the first and third tanks, the method further comprising maintaining a predetermined fluid level of the ultrasonically transmissive fluid in the first and third tanks by moving fluid to and from a fluid reservoir in fluid communication with the first and third tanks.

25. A method of ultrasonic imaging of a portion of patient anatomy using an ultrasonic transducer and an ultrasonic detector, the method comprising:

activating the ultrasonic transducer in a first tank containing the ultrasonic detector to generate ultrasonic signals, the first tank being filled with a selected ultrasonically transmissive fluid;

coupling ultrasonic signals through an ultrasonically transmissive first endwall between the first tank and a second tank, the second tank being positioned intermediate between the first tank and a third tank, the second tank having an access panel to permit access to the portion of the patient anatomy to be imaged, the method further comprising accessing the portion of the patient anatomy to be imaged via the access panel;

receiving the portion of the patient anatomy to be imaged in the second tank filled with the ultrasonically transmissive fluid;

coupling ultrasonic signals through an ultrasonically transmissive second endwall between the second tank and the third tank; and detecting ultrasonic signals with the ultrasonic detector in the third tank containing the ultrasonic detector, the third tank being filled with the ultrasonically transmissive fluid.

26. The method of claim 25, further comprising draining the ultrasonically transmissive fluid from the second tank wherein acoustical coupling between the ultrasonic transducer and the ultrasonic detector is maintained via the selected ultrasonically transmissive fluid in the first and third tanks and the portion of the patient anatomy to be imaged.

27. A method of ultrasonic imaging of a portion of patient anatomy using an ultrasonic transducer and an ultrasonic detector, the method comprising:

activating the ultrasonic transducer in a first tank containing the ultrasonic detector to generate ultrasonic signals, the first tank being filled with a selected ultrasonically transmissive fluid;

coupling ultrasonic signals through an ultrasonically transmissive first endwall between the first tank and a second tank, the second tank being positioned intermediate between the first tank and a third tank;

receiving the portion of the patient anatomy to be imaged in the second tank filled with the ultrasonically transmissive fluid;

coupling ultrasonic signals through an ultrasonically transmissive second endwall between the second tank and the third tank, at least one of the first and second endwalls is moveable, the method further comprising moving the at least one of the first and second endwalls to retain the portion of the patient anatomy to be imaged; and detecting ultrasonic signals with the ultrasonic detector in the third tank containing the ultrasonic detector, the third tank being filled with the ultrasonically transmissive fluid.

28. The method of claim 27 wherein movement of the moveable endwall causes a change in a volume of fluid contained in its respective tank, the method further comprising maintaining a predetermined fluid level of the ultrasonically transmissive fluid in the tank by moving fluid to and from a fluid reservoir in fluid communication with the tank coupled to the moveable endwall.

29. A method of ultrasonic imaging of a portion of patient anatomy using an ultrasonic transducer and an ultrasonic detector, the method comprising:

activating the ultrasonic transducer in a first tank containing the ultrasonic detector to generate ultrasonic signals, the first tank being filled with a selected ultrasonically transmissive fluid;

coupling ultrasonic signals through an ultrasonically transmissive first endwall between the first tank and a second tank, the second tank being positioned intermediate between the first tank and a third tank;

receiving the portion of the patient anatomy to be imaged in the second tank filled with the ultrasonically transmissive fluid;

coupling ultrasonic signals through an ultrasonically transmissive second endwall between the second tank and the third tank;

detecting ultrasonic signals with the ultrasonic detector in the third tank containing the ultrasonic detector, the third tank being filled with the ultrasonically transmissive fluid; and providing a visual indicator of the predetermined focal plane to indicate the predetermined focal plane with respect to an external portion of the patient anatomy.

* * * * *